United States Patent [19]

Iyengar et al.

[11] Patent Number: 5,952,411
[45] Date of Patent: *Sep. 14, 1999

[54] COMPOUND BEARING AN URETHANE LINKAGE WHICH IS AN ADDUCT OF RICINOLEIC ESTERS AND AN ISOCYNATE, USEFUL AS A PLASTICIZER FOR POLYVINYLCHLORIDE (PVC) AND A PROCESS FOR PREPARING SUCH COMPOUND

[75] Inventors: Srinivasan Subbagiri Ramaswamy Iyengar; Raut Kundalik Ganpat; Saxena Prabhat Kumar; Sivaram Swaminathan, all of Pune, India

[73] Assignee: C.S.I.R., New Delhi, India

[*] Notice: This patent issued on a continued prosecution application filed under 37 CFR 1.53(d), and is subject to the twenty year patent term provisions of 35 U.S.C. 154(a)(2).

[21] Appl. No.: 08/430,514

[22] Filed: Apr. 27, 1995

[51] Int. Cl.$^6$ .................................................... C08J 9/02

[52] U.S. Cl. .......................... 524/219; 524/567; 524/569; 560/25; 560/115

[58] Field of Search ................................. 524/219, 569, 524/567; 560/25, 115

[56] References Cited

U.S. PATENT DOCUMENTS

| | | | |
|---|---|---|---|
| 3,875,090 | 4/1975 | Levy | 524/557 |
| 4,569,972 | 2/1986 | Legue et al. | 525/129 |

*Primary Examiner*—Peter D. Mulcahy
*Attorney, Agent, or Firm*—Ladas & Parry

[57] ABSTRACT

A novel compound bearing urethane linkage of formula as shown herebelow, which is an adduct of ricinoleic ester and isocyanate, useful as a plasticizer for polyvinylchloride (PVC) and a process for the preparing the compound bearing urethane linkage by reacting fatty acid esters bearing hydroxyl groups with an organic isocyanate in the presence of a catalyst at a temperature in the range of 30°–100° C.

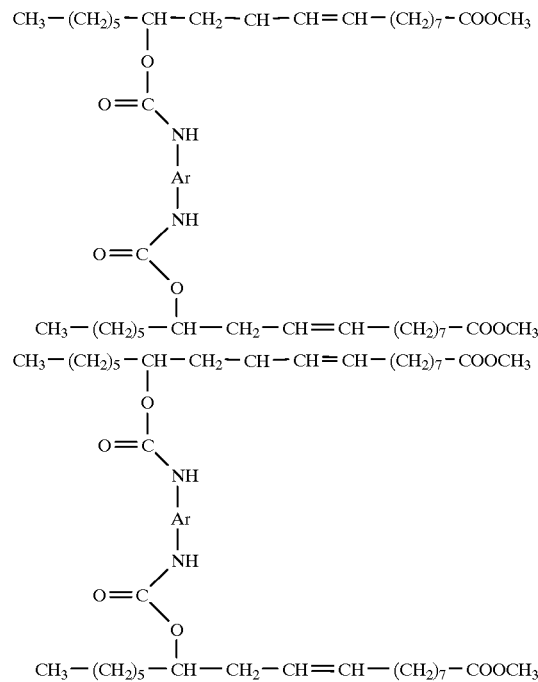

Wherein Ar=

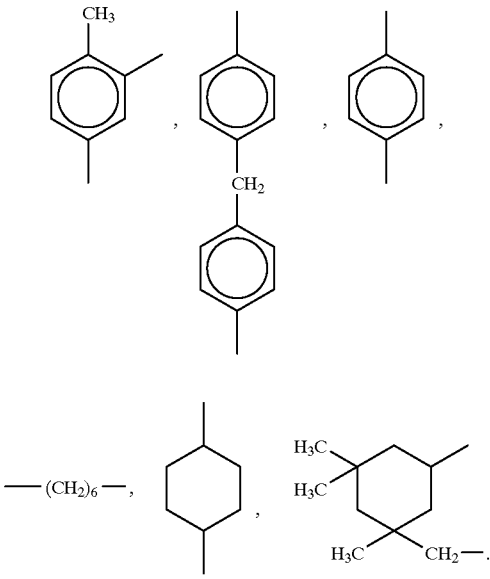

1 Claim, No Drawings

COMPOUND BEARING AN URETHANE LINKAGE WHICH IS AN ADDUCT OF RICINOLEIC ESTERS AND AN ISOCYNATE, USEFUL AS A PLASTICIZER FOR POLYVINYLCHLORIDE (PVC) AND A PROCESS FOR PREPARING SUCH COMPOUND

This invention relates to a novel compound bearing an urethane linkage useful as a plasticizer for polyvinyl chloride (PVC) and a process for preparing the compound. This compound is an adduct of ricinoleic esters and an isocyanate, which is prepared by the process of the present invention is new and has formula 1.

(FORMULA 1)

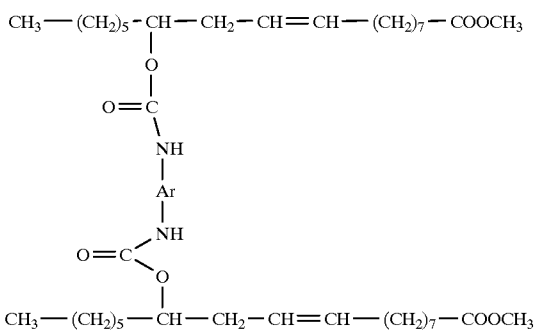

wherein Ar is selected from the group consisting of

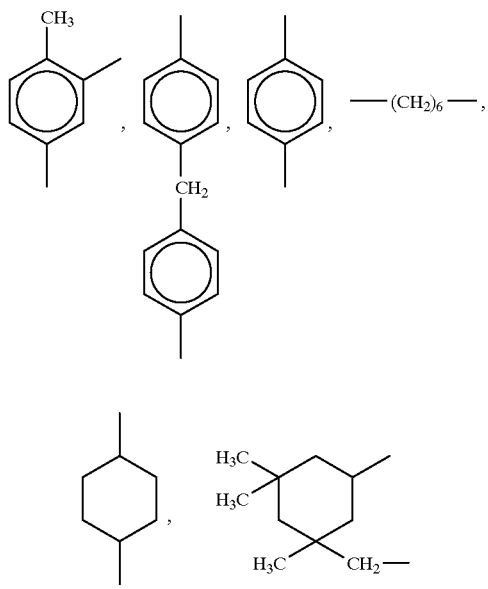

The invention specifically relates to a process for the preparation of a compound bearing an urethane linkage useful as a plasticizer for poly vinylchloride (PVC). The compound prepared by the process of the present invention is new and has the formula 1. The compound of formula 1, is derived from a fatty acid ester bearing a hydroxyl functionality and/or compound containing isocyanate functionality. More specifically, the invention relates to a process for the preparation of urethane type compound of formula 1 having molecular weight in the range of 650 to 900.

The compound of formula 1, prepared by the process of the present invention has excellent compatibility with PVC on account of the desirable functional groups present in the molecule. Hence, the invention further provides a process for the preparation of improved compounded PVC employing the urethane type compound of formula 1.

It is well known in the prior art that addition of organic compounds, called plasticizers, to PVC confers on the PVC desirable properties such as flexibility, softness, good feel and ease of processability, extensibility and lower melting temperature [Encyclopedia of PVC Vol. 1 and 2, L. I. Nass (1976)]. Plasticizers function by dissolving in PVC, reducing the cohesive energy density between the polymer chains and reducing the polar forces exerted by the halogen atoms present in PVC. For any organic compound to function as an effective plasticizer for PVC it must possess (a) very high miscibility with PVC, (b) must have polar groups and (c) must have a low tendency to diffuse and migrate out of the polymer during its effective service life. In addition, the plasticizer must not cause colouration to PVC, should be non toxic, odorless, possess low volatility and thermally stable at the temperature of mixing and compounding PVC with plasticizer.

A variety of organic compounds have been reported as effective plasticizers for PVC. These include esters of phthalic anhydride with aliphatic alcohols (linear/branched) with four to fifteen carbon atoms, epoxidized soyabean oil, esters of trimellitic acids, phosphates, esters of benzoic and citric acids, and halogenated hydrocarbons. Higher molecular weight polyesters (800–6000) prepared by condensation of diols with adipic or sebacic acids are also used as plasticizers. Of these, phthalate based plasticizers are the most widely used because of their excellent compatibility with PVC, ease of fusion and all round desirable properties.

Nevertheless, phthalate esters are not without drawbacks. Dioetylphthalate has been implicated as a carcinogen causing liver cancer in rats. Their molecular weights are low on account of which they diffuse out of PVC rapidly and cause "fogging" (cloudy dsposits) of glasses and other transparent surfaces. They are easily extracted by organic solvents, making them unsuitable for use in solvent contact applications. They produce PVC products whose surface resistivity is very high (approximately $4 \times 10^{14} \Omega$ at 30° C.) for many applications such as antistatic products for hospitals flooring materials, footwear, hoses, clean room fixtures, trays for integrated circuits and floppy discs, conveyor belt etc. The surface resistivity can be brought down by a factor of $10^1$–$10^2$ by adding an antistat additive (example Irgastat 51 of Ciba Geigy). However, use of such additives leads to loss of desirable properties of PVC. The thermal and light stability is adversely affected and the antistatic additive exudes out of PVC.

To overcome the above problems envisaged in the prior art, the applicants have now provided a novel compound bearing an urethane linkage shown in formula 1, which is useful as a plasticizer for PVC; a process for preparing such compound and, a manner in which a compounded PVC is prepared by employing the novel compound.

Therefore, one object of the present invention is to provide a compound having an urethane linkage of formula 1.

Another object of the invention relates to a process for the preparation of new plasticizer for PVC.

Yet another object of the present invention is to provide a process for the preparation of new plasticizer derived from fatty acid esters and a hydroxyl group, and an isocyanate bearing organic compound.

Still another object of the present invention is to provide a process for the preparation of improved compounded polyvinyl chloride using the compound of formula 1 as a primary plasticizer. The use of compound of formula 1 in conjunction with PVC confers on PVC many desirable properties such as flexibility, softness, good mechanical and thermal properties. In addition, use of compound of formula 1 eliminates many of the drawbacks of the hitherto known plasticizers for PVC.

Further object of the invention is for a compounded PVC comprising polyvinyl chloride and a plasticizer of formula 1.

In the course of the applicants research, they have developed a process for the preparation of a new organic compound of the formula 1 which show useful properties as primary plasticizer for PVC. The compound of formula 1 is derived from the reaction of fatty acid esters having eighteen carbon atoms and a hydroxyl group, and organic isocyanates.

The fatty acid esters suitable for the present invention are esters of ricinoleic acid and 12 hydroxyl stearic acid. The ester can be derived by reacting ricinoleic acid or 12 hydroxystearic acid with an alcohol having a linear or branched alkyl group having 1–10 carbon atoms.

The isocyanate useful in the process of the present invention can be selected from any organic isocyanates having one or two isocyanate groups per molecule. Examples are toluene diisocyanate of formula 3,

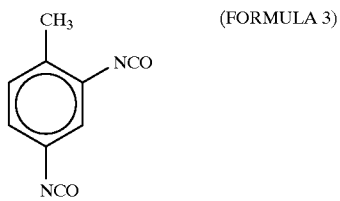
(FORMULA 3)

4,4'-diisocyanatodiphenylmethane of formula 4,

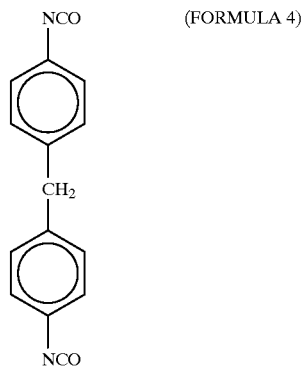
(FORMULA 4)

1,4-diisocyanatobenzene of formula 5,

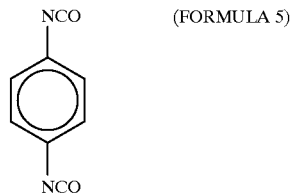
(FORMULA 5)

hexamethylene diisocyanate of formula 6,

OCN—(CH$_2$)$_6$—NCO    (FORMULA 6)

isophorone diisocyanate of formula 8,

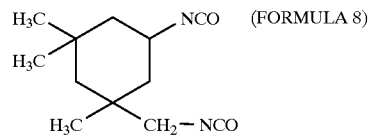
(FORMULA 8)

1,4-diisocyanatocyclohexane of formula 7.

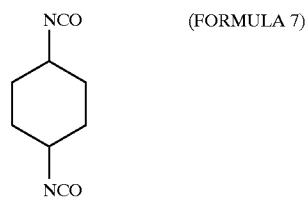
(FORMULA 7)

The preferred isocyanates are those derived from aromatic compounds and having at least two isocyanate groups.

Accordingly, the present invention provides a novel compound bearing urethane linkage having formula 1.

The invention also provides a process for the preparation of a compound bearing urethane linkage having formula 1 useful as a plasticizer for PVC which comprises reacting fatty acid esters bearing hydroxyl groups with an organic isocynate at a temperature in the range of 30–100° C. in the presence of a catalyst. The molar ratio of hydroxyl bearing fatty acid to the isocyanate may be in the range of 2:1.1, the preferred ratio being 2:1.05. The catalyst employed in the reaction may be selected from any one of the following: di-n-butyltindilaurate, di-n-butyl-tinoxide, 1,4-diazabicyclo [2.2.2] octane (DABCO), 4', 4'-dimethylamino pyridine (DMAP) and 1, 8-diazabicyclo [5.3.0] undec—7—ene (DBU). The concentration of the catalyst may range from 0.02–0.2% by weight of the isocyanate compound. The preferred concentration is in the range of 0.05%. The reaction is conducted for a period of 1–3 hours. The progress of the reaction is monitored by Brookfield viscosity and determination of hydroxyl number. The final product should have a viscosity below 2500 centipoises at 27° C. and have a hydroxyl number below 20 (expressed as mg KOH/g). The product molecular weight as measured by vapour pressure osmometry is in the range of 650–900 depending on the nature of the isocyanate.

The process of preparing the plasticizer is clean, does not produce any effluents or by-products and is ready for use at the end of the reaction directly without any further processing.

The structures of the compounds prepared by the process of the present invention have been established by a variety of spectroscopic techniques such as infra red, nuclear magnetic resonance and mass spectrum. More specifically, a product derived from the reaction of ricinoleic acid methyl ester with toluene diisocyanate shows in infra red spectrum absorption at 3320, 1730–1750, and 1400–1600 inverse centimeters due to —NH, carbonyl and —HC=CH— groups. The nuclear magnetic resonance shows peaks at 0.9–2.5, 3.6–3.7, 5.0–6.0 and 6.5–7.5 ppm corresponding to the methyl groups, methoxy group, vinylic hydrogen and aromatic hydrogen attached to ring.

The invention further provides a process for the preparation of a compounded PVC, which process comprises mixing a compound of formula 1 at a temperature in the range of 120° to 150° C. and in the presence of a stabiliser and if desired, preparing the sheets of the compounded PVC, so prepared, of the desired dimensions by conventional methods.

The advantages of using the compound of the formula 1 are:

1. The compound is compatible with both PVC and phthalate type plasticizers, enabling its use either by itself as a primary plasticizers or in blends with phthalates, if necessary.
2. It has a high molecular weight and thus low tendency to migrate or exude from the surface.
3. It is derived from naturally occurring fatty acids and possess urethane type linkages, which has been established in the prior art as biocompatible (Ref: Japan Patent 7650,958 dated May 6, 1976 to Dainippon Ink and Chemicals Inc.). Hence, the plasticizer should show very low toxicity.
4. Its polar character makes it poorly soluble in organic solvents. Hence PVC plasticized by compounds of formula 1 show excellent resistance to extraction by organic solvents.
5. PVC plasticized by plasticizers of formula 1 show exceptionally low surface resistivities ($6 \times 10^9 \Omega 30°$ C.) without addition of any antistatic additives.

The plasticizer, prepared by the process as described above is compounded with PVC in an electrically heated two roll mill in presence of stabilizers to form a smooth sheet of 150 mm×150 mm×2 mm size. The content of plasticizer used may be in the range of 40 to 60 parts per hundred parts of the resin (phr). The preferred composition is 50 phr. The urethane plasticizer can also be incorporated in blends with ester type plasticizers well known in the prior art. For example, urethane plasticizer can be blended with di-2-ethylhexylphthalate (DOP) in an amount ranging from 10:90 to 90:10 proportions prior to incorporation in PVC. The stabilizers added are chosen from a variety of metal stearates well known in prior art. The metal stearates can be derived from barium, cadmium, calcium, zinc and the like. The concentration of the stabilizers is in the range of 1–5 phr, preferred concentration being 3 phr. The dry blend of PVC, plasticizer and the stabilizers are mixed in a two roll mill at the temperature range 120–150° C. for 2–10 minutes, till complete and uniform fusion of the blend occurs. The sheet is then used for preparing test specimens which are tested for properties as per methods prescribed by American Society of Testing Materials (ASTM). The results are shown in Table 1 where the performance of the urethane plasticizer is compared with di-2-ethylhexylphthalate (DOP) under identical conditions (Table 1). The mechanical as well as high and low temperature properties of urethane and DOP plasticizers are essentially similar. However, dramatic improvements are observed with regard to extractability in organic solvents and surface resistivity. The results confirm that the compound of formula 1, is a primary plasticizer for PVC and possesses useful properties which are not present in DOP type plasticizers.

TABLE 1

COMPARATIVE PROPERTIES OF COMPOUNDED PVC USING URETHANE PLASTICIZER AND DOP[a]

| Property | Test method | Unit | Value Urethane[b] | DOP[c] |
|---|---|---|---|---|
| Hardness, Shore A | ASTM D-2240 | — | 78 | 79 |
| Tensile strength | ASTM D-412 | kg/cm$^2$ | 220 | 212 |
| Modulus, 100% | ASTM D-412 | kg/cm$^2$ | 133 | 131 |
| Elongation at break | ASTM D-412 | % | 370 | 340 |
| Surface resistivity 30° C. | BS 2050 | Ω | $6 \times 10^9$ | $3.8 \times 10^{14}$ |
| Glass transition temperature | | ° C. | −26 | −31 |
| Heat loss at 130° C., 3 hr | | % | 0.8 | 0.6 |
| Extraction test, wt. loss | ASTM D-1239 | | | |
| i) Water, 35° C. 24 hr | | % | 0.3 | 0.03 |
| ii) Kerosene, 24 hr | | % | 2.6 | 44 |

[a]PVC resin (K = 65), 100 phr, compounded with plasticizer 50 phr and stabilizers 3 phr; sheet thickness: 30–35 mil.
[b]Compound of formula 1 prepared by the reaction of ricinoleic acid with toluene-diisocynate.
[c]Di-2-ethylhexylphthalate The invention is described in detail in the examples which are provided by way of illustration only and therefore should not be construed to limit the scope of the invention.

Examples 1 to 5 relate to the preferred processes for preparing a few compounds bearing urethane linkage and examples 6 to 9 are for the preferred processes of preparing plasticized PVC.

EXAMPLE 1

In a 2 liter four neck round bottom flask equipped with mechanical stirrer, thermowell, gas bubbler and dropping funnel two moles of methyl ricinoleate of formula 9

(FORMULA 9)

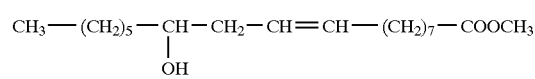

and 0.5 g of dibutyl tin dilaurate are taken. The flask is mounted in a 2 L capacity heating mantle, the heating of which can be suitably controlled. With continuous stirring in a stream of nitrogen has 0.9 mole of toluene diisocyanate (TDI) of formula 3 is added dropwise from the dropping funnel, care being taken not to allow the temperature of the reaction flask to increase above 30° C. After the addition of TDI is over which lasts for about an hour, the contents of the flask are heated to 70° C. and maintained at 70° C. for one hour. As soon as addition of TDI is over, a sample is drawn for percentage isocyanate determinations. Two more samples, one after half an hour and another after one hour after the complete addition of TDI are drawn for percentage isocyanate determination. It is observed to decrease periodically and reaches minimum after about one hour heating at 70° C. Viscosity of the material is observed to increase during the course of the reaction and heating is stopped after one hour at 70° C. The colour, acid value, —OH value, viscosity and molecular weight of the product which is a Benzene, 2, 4 diisocyanato-1-methyl adduct and 9-octa decenoic-12 hydroxy methyl ester of the formula 1 wherein Ar represents formula 3, are observed to be 200 (APHA), 0.25 mg.KOH/gm, 18 mg.KOH/gm, 2,400 centipoises and 850 respectively.

EXAMPLE 2

In a 2 (liter) four neck round bottom flask equipped with mechanical stirrer, thermowell, gas bubbler and dropping

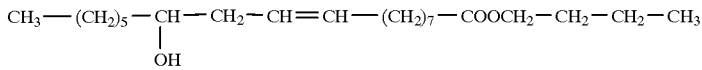

(FORMULA 11)

funnel 2.1 moles of 12-hydroxy methyl stearate of formula 10

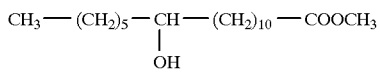

(FORMULA 10)

and 0.35 g of di-n-butyl-tin dioxide are taken. The flask is mounted in a 2 L capacity heating mantle, the heating of which can be suitably controlled.

With continuous stirring and in a stream of $N_2$ gas, one mole of toluene diisocyanate of formula 3 is added dropwise through the dropping funnel, care being taken not to allow the temperature of the reaction mixture to exceed 30° C. After the addition is over, which lasts for about an hour, a sample of the reaction mixture is withdrawn for percentage isocyanate determination and the flask is heated to 70° C. and maintained at 70° C. After half an hour at 70° C., another sample is drawn for % NCO and hydroxyl value determination. Similarly after heating at 70° C. for one hour anothersample (benzene 2.4 diisocyanate-1-methyl adduct of octadecenoic-12-hydroxy methyl ester of formula 2)

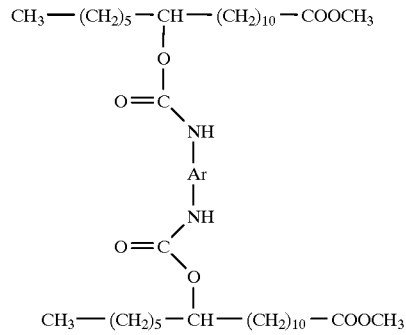

(FORMULA 2)

is drawn for percentage isocyanate and hydroxyl value determination. After total heating period of one hour at 70° C. the contents are cooled and the product of formula 2 which is a Benzene 2, 4 diisocyanato-1-methyl adduct of octa decenoic acid 12-hydroxy methyl ester of formula 2 analysed for colour, acid value, hydroxyl value, viscosity and molecular weight which are found to be 150–200 (an index of color as specified by American Public Health Association-APHA), 0.3 mg.KOH/gm, 12 mg.KOH/gm, 1480 centipoises and 855 respectively.

EXAMPLE 3

In 1 L (liter) four neck round bottom flask equipped with mechanical stirrer, thermowell, gas bubbler and dropping funned two moles of butyl ricinoleate of formula 11 and 0.35 g of dibutyl tin-dilaurate are weighed and the flask is mounted in a 1L capacity heating mantle, of which heating can be suitably controlled. Then with continuous stirring, in a stream of nitrogen gas, 0.95 mole of toluene diisocyanate of formula 3 of the drawings is added dropwise through the dropping funnel. The additionwhich lasts for about 40 minutes is carried out maintaining the temperature of the flask below 30° C. After the addition is over the flask is heated to 70° C. and maintained at 70° C. for one hour. During this period of one hour two samples are drawn at the interval of 30 minutes each for percentage isocyanate and hydroxyl value. Both % NCO, as well as —OH value are observed to decrease whereas viscosity of the contents is observed to increase during the course of his reaction. After one hour heating at 70° C., the contents benzene 2.4-diisocyanate-1-methyl adduct of 9-octadecenoic and 12-hydroxy butyl ester are cooled, discharged in a stoppered container and the compound of the formula 1 which is analyzed for colour, acid value, hydroxyl value, % NCO viscosity and molecular weight, which are observed to be 200 APHA, 0.71 mgKOH/gm, 10.79 mgKOH/gm, 0.83, 1920 centipoises (27 C) and 750 respectively.

EXAMPLE 4

In a 500 mL capacity four neck round bottom flask equipped with mechanical stirrer, thermowell, gas bubbler and dropping funnel 350 gm butyl ricinoleate of formula 11 and 0.35 g of dibutyl tin dilaurate are taken and the flask is mounted in a constant temperature oil bath, the temperature of which can be suitably controlled. From the dropping funnel 111.0 g iso-phorone diisocyanate (IPDI) of formula 8 is added dropwise with continuous stirring in a stream of nitrogen gas. The addition which lasts for about an hour is done at 27° C. After the addition is over, the contents i.e. 3-isocyanato methyl 3, 5, 5-timethyl-cyclo-hexyl isocyanate adduct of butyl ricinoleateare heated to 70° C. and maintained at 70° C. for one hour, after which the flask is cooled to room temperature and the compound of the formula 1 viscosity and molecular weight which are found to be 50 APHA, 0.5 mg KOH/gm, 15 mg KOH/gm, 0.5, 2200 centipoise (27° C.) and 820 respectively.

EXAMPLE 5

In a 500 mL capacity four neck round bottom flask equipped with mechanical stirrer, thermowell, gas bubbler and dropping funnel 0.22 moles methylricinoleate of formula 9 of the drawings and 0.04 gm of dibutyl tin oxide are taken. The flask is mounted in a constant temperature oil bath and with continuous stirring, in a stream of $N_2$, gas 0.1 moles of hexamethylene diisocyanate of formula 6 is added dropwise through the dropping funnel, temperature of the flask being maintained below 30° C. during the course of addition. After the addition is over, the contents i.e. hexamethylene isocyanate adduct of methyl ricinoleate are heated to 50° C. for one hour and then cooled to room temperature and the compound of the formula 1 analysed for colour, acid value, hydroxyl value, % isocyanate, viscosity and molecular weight, which are found to be 50 APHA, 0.4 mg KOH/gm, 21,2 mg KOH/gm, 0.32, 1800 centipoises (27° C.) and 800 respectively.

EXAMPLE 6

In a 250 mL beaker, 50 g of polyvinyl chloride of K-65 grade, 25 g of plasticizer derived from toluene diisocyanate and methylricinoleate (from ex:1), 0.5 g stearic acid and 1.5 g of Ba—Cd stearate as stabilizer are weighed and mixed thoroughly with the help of a spatuala. Then the material is mixed in a two roll PVC mixing mill for 5 minutes. The rolls are maintained at 140±2° C. during mixing. After complete fusion of PVC and thorough mixing of plasticizer and stabilizer, a continuous band is obtained on the roll which is cut repeatedly horizontally and mixed thoroughly. A continuous sheet of about 3 to 4 mm is obtained at the end.

From this, a smooth sheet of 150 mm×150 mm×2 mm size was obtained by compression moulding in a hydraulic press at 165° C. for five minutes. The test specimens for mechanical property evaluation were cut using suitable die as per American Society of Testing Materials (ASTM) D—412. The hardness, tensile strength, 100% modulus, elongation at break of the compounded PVC sheet are found to be 78 (shore A) 220 kg/cm$^2$, 133 kg/cm$^2$ and 370% respectively.

EXAMPLE 7

In a 250 mL beaker 120 g polyvinyl chloride powder of K–65 grade, 41 g of a plasticizer derived from toluene diisocyanate and methyl ricinoleate, 1.2 g stearic acid and 2 g of Ba—Cd stearate as the stabilizer are weighed and mixed thoroughly with the help of a spatuala. Then the mixture is compounded by milling in a two roll PVC mixing mill at 140±2° C. for five minutes. Initially the material softens on the heated rolls and fuses to form a band around one of the rolls of the mill. The band is cut repeatedly by a knife in horizontal direction and the sheet is obtained repeatedly. After forming a smooth, band, it is cut and an uniform sheet of about 3 to 4 mm thickness is obtained.

This sheet is used for compression moulding (at 165° C. for five minutes at 1800 psi pressure) to set an uniform smooth sheet of 150 mm×150 mm size.

The test specimens for the property evaluation were punched out from this sheet. Using suitable die as per American Society of Testing Material (ASTM) D—412, and were found to give Shore A hardness, tensile strength, 100% modulus and elongation at break as 80, 262.5 kg/cm$^2$, 187.1 kg/cm$^2$ and 300% respectively.

EXAMPLE 8

In a 250 mL capacity beaker 100 g polyvinyl chloride powder of K–65 value, 44 g of urethane plasticizer, derived from toluene diisocyanate and methylricinoleate, 2 g of Ba—Cd stearate stabilizer and 1 g of stearic acid as the lubricant are weighed and mixed thoroughly by stirring with the help of spatuala. The contents of the beaker are milled in a two roll PVC mixing mill at 140° C. for five minutes. The rolls of the mill are heated electrically. Initially the PVC powder softens while in contact with the rolls and on complete fusion it forms a continuous band over one of the rolls. The continuous band is cut repeatedly and mixed thoroughly to give good dispersion of plasticizer and stabilizer in the PVC sheet. Finally, by having a horizontal cut, continuous, uniform sheet of the compounded material having 3 to 4 mm thickness is obtained.

A suitable sheet of size 150 mm×150 mm×2 mm is obtained by compression molding of the compounded sheet for five minutes at 165° C. and at 2000 psi.

The test specimens for property evaluation were punched out from the sheet using suitable dies as per ASTM specifications. The Shore A hardness, tensible strength, 100% modulus and elongation at break were found to be 78, 225 kg/cm$^2$, 132 kg/cm$^2$ and 330% respectively.

EXAMPLE 9

In a 500 mL beaker 140 g of polyvinyl chloride (PVC) powder of K-65 value, 77 g of urethane plasticizer, derived from toluene diisocyanate and methylricinoleate, 4 g of Ba—Cd stearate as stabilizer and 1 g of stearic acid as lubricant are weighed and thoroughly mixed by stirring with spatuala. The contents are milled in a two roll PVC mixing mill at 140° C. for five minutes. A uniform sheet is formed on one of the rolls after softening, and fusion of PVC with the plasticizer and stabilizer which is cut horizontally several times and milled to get good sheet of 3 to 4 mm thickness. This sheet is used to get uniform and smooth sheet of 150 mm×150 mm×2 mm size by compression moulding at 165° C. for 2 minutes and at 1800 psi pressure. The test specimens for property evaluation were punched out using suitable die as per ASTM and the properties such as Shore A hardness, tensile strength, 100% modulus and elongation at break were observed to be 75, 220 kg/cm$^2$, 133 kg/cm$^2$ and 390% respectively.

We claim:

1. A composition of matter consisting essentially for a novel compound of the following formula:

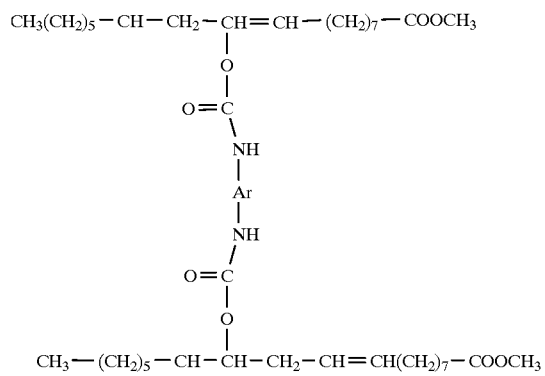

wherein Ar is selected from the group consisting of [Ar=]
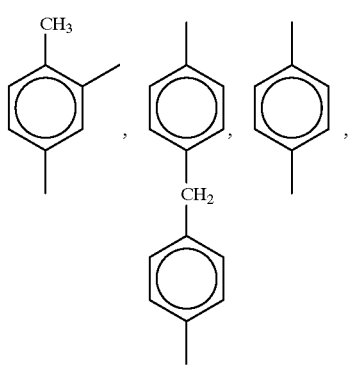
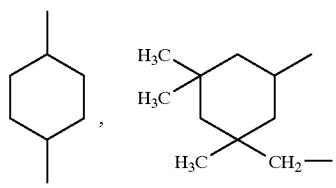
which is an adduct of ricinoleic acid and an isocyanate.
* * * * *